Figure 1:
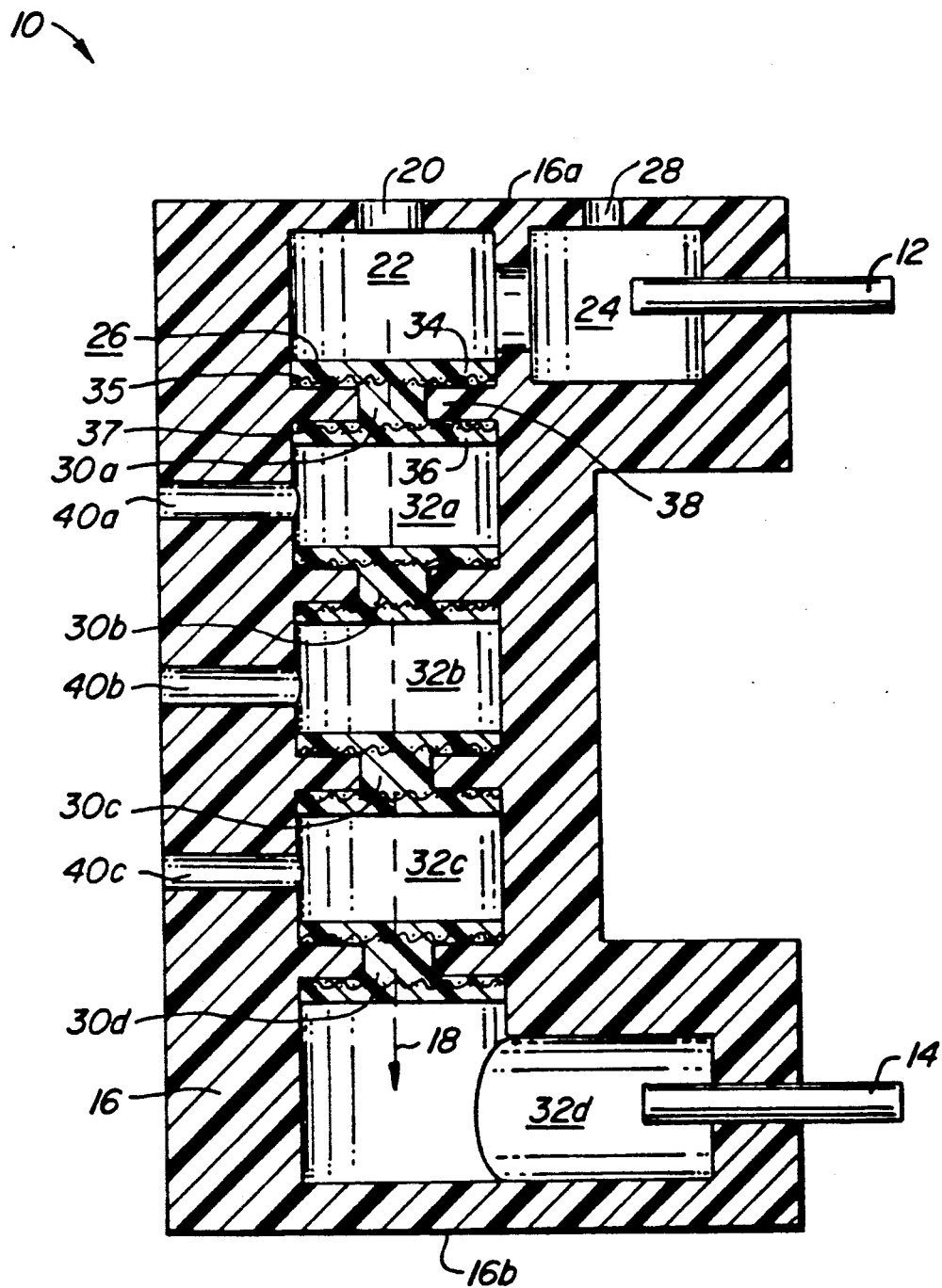

United States Patent [19]
Manning et al.

[11] Patent Number: 5,078,853
[45] Date of Patent: Jan. 7, 1992

[54] SEGMENTED ELECTROPHORETIC SEPARATION SYSTEM USEFUL FOR LIPID PROFILING

[75] Inventors: Charles R. Manning, Palo Alto; LeRoy J. Pinto; Joyce Chang, both of Los Altos, all of Calif.

[73] Assignee: Assay Technology, Inc., Palo Alto, Calif.

[21] Appl. No.: 673,640

[22] Filed: Mar. 22, 1991

[51] Int. Cl.⁵ .............................................. G01N 27/26
[52] U.S. Cl. ........................... 204/299 R; 204/182.8; 436/71
[58] Field of Search .................. 204/299 R, 182.8; 436/71

[56] References Cited

U.S. PATENT DOCUMENTS

| | | | |
|---|---|---|---|
| 3,620,947 | 11/1971 | Allen et al. | 204/182.8 |
| 3,844,925 | 10/1974 | Stathakos | 204/182.9 |
| 4,189,370 | 2/1980 | Boschetti | 204/182.8 |

FOREIGN PATENT DOCUMENTS

0384067A2  8/1990  European Pat. Off. .

OTHER PUBLICATIONS

Cobb and Sanders, "Enzymic Determination of Cholesterol in Serum Lipoproteins Separated by Electrophoresis", *Clin. Chem.*, 24/7, 115–1120 (1978).
Muniz, "Measurement of Plasma Lipoproteins by Electrophoresis on Polyacrylamide Gel", *Clin. Chem.*, 23/10, 1825–1833 (1977).
Serwer, "Agarose Gels: Properties and Use for Electrophoresis", *Electrophoresis*, vol. 4, pp. 375–382 (1983).
Serwer et al., "Agarose Gel Electrophoresis of Bacteriophages and Related Particles . . .", *Electrophoresis*, vol. 4, 233–236 (1983).

*Primary Examiner*—T. Tung
*Assistant Examiner*—David G. Ryser
*Attorney, Agent, or Firm*—Majestic, Parsons, Siebert & Hsue

[57] ABSTRACT

A diagnostic device is provided where the preferred embodiment is useful for sorting seric or plasmatic lipoproteins into four cholesterol fractions. The device comprises a plurality of gel matrixes, preferably agarose-based, defining a liquid pathway upon which a directioinal electrophoretic gradient can be imposed. The gel matrixes are in a serial relationship and preferably are of a successively decreasing pore size from a most upstream matrix to a most downstream matrix. In a preferred embodiment the three more downstream gel matrixes are in a noncontiguous relationship and are separated by interfaces containing buffer. These interfaces are adapted to receive a separate lipoprotein fraction upon reversal of the electrophoretic gradient direction.

12 Claims, 2 Drawing Sheets

SEGMENTED ELECTROPHORETIC SEPARATION SYSTEM USEFUL FOR LIPID PROFILING

FIELD OF THE INVENTION

This invention relates to the electrophoretic separation of charged particles, and more specifically, relates to the electrophoretic fractionation and quantitative analysis of macromolecules, such as the lipid constituents of human serum for diagnostic purposes.

BACKGROUND OF THE INVENTION

Fractionation and quantitative analysis of charged particles such as macromolecules has traditionally been a slow and expensive process. Tests utilizing immunochemistry have been successfully applied to single component analysis of substances having requisite properties, but these methods have not been applicable to separation and quantitation of multiple proteins species from a single sample. Such determinations continue to be carried out by electrophoresis (i.e., differential migration of charged molecules in an electrical field) which continues to be regarded as a high resolution research method not applicable to high volume testing.

Measurement of the level of cholesterol in human serum is one of the most commonly ordered diagnostic procedures. It is believed to be highly predictive of the probability of occurrence of coronary heart disease (CHD). Despite the fact that the National Cholesterol Education Program has stated that determination of the overall lipid profile (i.e., the specific distribution of the total cholesterol among its HDL, LDL, VLDL, and chylomicron forms) is more predictive of CHD than total cholesterol measurement, the number of lipid profile determinations carried out remains relatively small compared to the number of total cholesterol tests. This is largely due to the relative difficulty and expense of carrying out accurate lipid profile tests. Lipid profile tests have been conducted by ultracentrifuge, gel chromatography, fractional precipitation, and electrophoretic methods, but these have not been found to be cost effective and convenient for high volume testing outside of the laboratory.

Electrophoresis is applicable to these problems and continues to be a popular and powerful method for analyzing charged macromolecules despite its complexity. Variants of electrophoresis have been developed over the years which sought to incorporate the physical advantages of certain states and configurations of matter. Among these, gel, thin film, and capillary electrophoresis have made notable contributions in biochemical analysis.

Use of gels as electrophoretic media minimizes the convective and diffusive randomization of bands promoting more rapid separations. Thin film and capillary techniques have made use of thin layers allowing greater heat transfer, hence more rapid separation through the use of higher voltages. Despite their advantages in a research environment, these techniques have remained esoteric and difficult to implement outside a laboratory setting.

Current clinical methods for separating HDL (high density lipoprotein), LDL (low density lipoprotein), and VLDL (very low density lipoprotein) cholesterol fractions include ultracentrifugation, gel chromatography, fractional precipitation, and electrophoresis.

Ultracentrifugation is considered a reference method since the designations HDL, LDL, and VLDL actually refer to density fractions separated by centrifuge; however, overnight processing is required for each centrifugation step. Gel chromatography correlates well with centrifugal analysis and is more rapid, but requires equally exotic equipment and expertise.

Fractional precipitation is the most commonly used method for lipid profiling in the conventional clinical laboratory. This procedure is reasonably convenient in a laboratory setting, but has shortcomings in validity and accuracy. In the fractional precipitation procedure, LDL cholesterol is calculated from the equation:

$$[LDL\ \text{Cholesterol}] = [\text{Total Cholesterol}] - [HDL\ \text{cholesterol}] -$$
$$[VLDL\ \text{Cholesterol}] - [\text{Chylomicron Cholesterol}].$$

A direct analysis is performed for total cholesterol, HDL cholesterol, and triglycerides. HDL cholesterol is analyzed by fractional precipitation followed by enzymatic assay of the supernatant solution, while total cholesterol and triglycerides are analyzed directly by conventional enzymatic methods. VLDL cholesterol is assumed to be equal to 1/5 (triglycerides) and chylomicron cholesterol is assumed to be zero in fasting patients.

Thus, the fractional precipitation method commonly used has several disadvantages. First, it is based on assumptions that are only approximately correct under fasting conditions. Second, it requires a fasting patient. Third, it requires three separate analytical procedures which require independent calibration. Fourth, it is not easy to perform outside a laboratory environment.

Muniz (of Ames Co., a division of Miles Laboratories) has described a method for separating cholesterol fractions by conventional electrophoresis. *Clin. Chem.* 23/10, pp. 1826–1833 (1977), where a homogeneous running gel of polyacrylamide is used to run samples of plasma. The chylomicron fraction remained in the sample gel, the VLDL were retained near the origin of separation gel, and the LDL and HDL fractions were bands in the separation (or running) gel. Quantitation of the separate fractions is not readily obtained from such a system because the gels are fragile and cannot be removed.

Cobb and Sanders (of Helena Laboratories) described a method for quantitating separated cholesterol fractions from a thin layer electrophoresis plate, *Clin. Chem.* 24/7, pp. 1116–1120 (1978). The authors report having used cellulose acetate plates on a plastic backing; but this procedure is laborious, imprecise, and does not allow quantitation of VLDL cholesterol in many cases.

Boschetti (U.S. Pat. No. 4,189,370, issued Feb. 19, 1980) described a method for separation of cholesterol fractions using two different, contiguous electrophoretic zones in a thin layer configuration. This procedure separated only two of the four cholesterol fractions, and did not provide for quantitation of separated fractions.

Allen (U.S. Pat. No. 3,620,947, issued Nov. 16, 1971) described an electrophoretic device with a plurality of contiguous zones. This device did not demonstrate high resolving power for proteins, and no means was provided to allow removal of separated fractions for quantitation.

Stathkos (U.S. Pat. No. 3,844,925, issued Oct. 29, 1974) described an isoelectric focusing column with a plurality of particle bed zones interposed between liquid regions with ports for sampling. The particle beds were of identical composition and served as locations for developing the pH gradients required for isoelectric focusing. This device provided a sampling scheme for proteins having different isoelectric points but did not have size separation properties.

To date only ultracentrifuge and gel chromatography methods have afforded a complete separation of all cholesterol fractions, but a simple, convenient device or system for a total and direct lipid profile separation and analysis from a single sample has not been achieved.

In the Drawings

Figure 2:
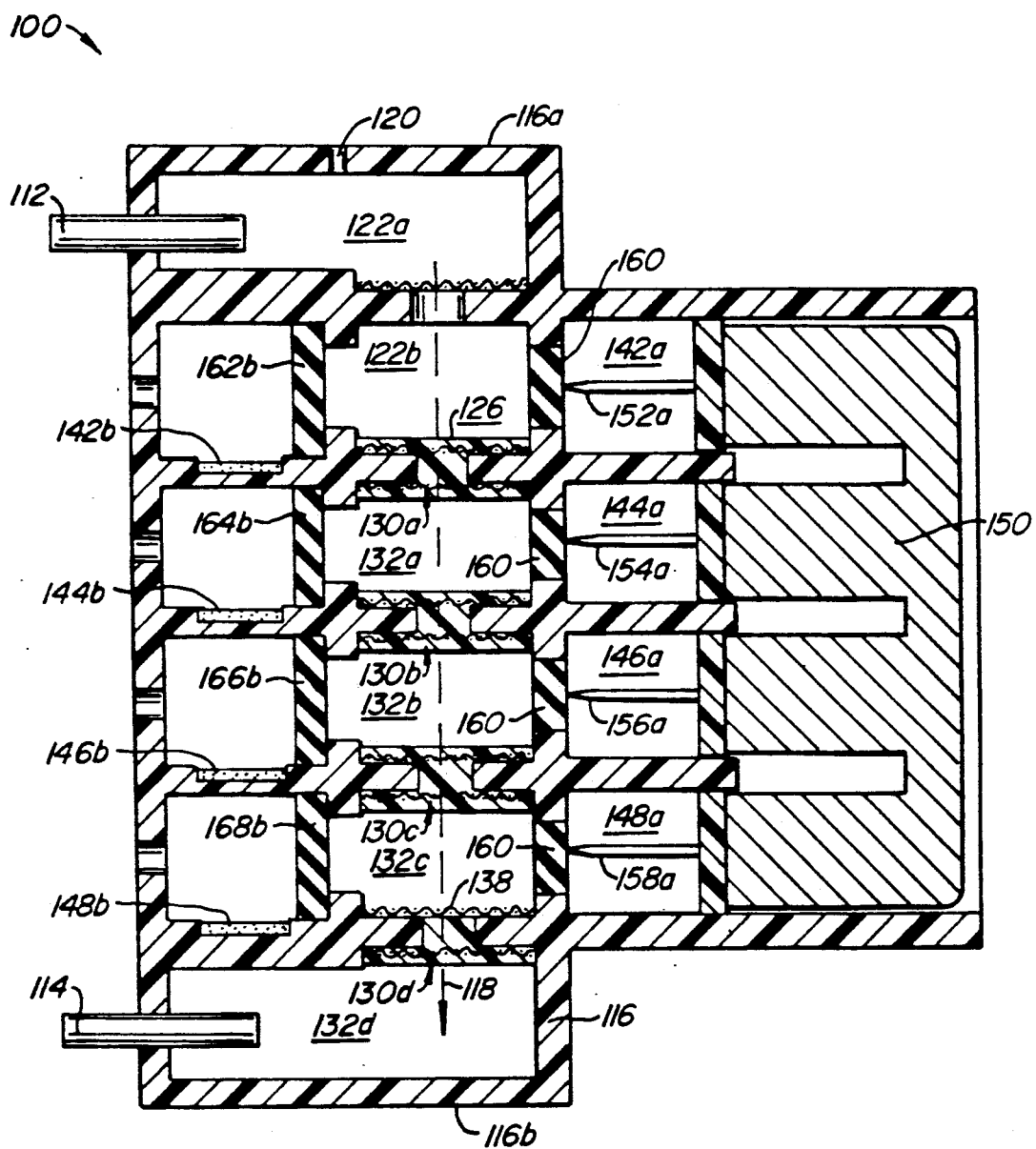

FIG. 1 illustrates a side, cross-sectional view of one embodiment of the present invention; and FIG. 2 illustrates a side, cross-sectional view of another embodiment of the invention.

SUMMARY OF THE INVENTION

It is an object of the present invention to provide a diagnostic apparatus useful for electrophoretic fraction of charged particles, such as the four cholesterol fractions from a serum sample, in a simple, convenient system, particularly so that a total and direct lipid profile separation and analysis can be achieved in a cost-effective manner.

In one aspect of the present invention, a diagnostic apparatus useful for electrophoretic fractionation of charged particles, including macromolecules, having different molecular weights in a liquid sample comprises a plurality of gel matrixes, means for introducing the liquid sample, and a plurality of collecting means. The gel matrixes define a liquid pathway upon which a directional electrophoretic gradient can be imposed, such as when the liquid sample is introduced. The collecting means are disposed in the liquid pathway and associated with gel matrix boundaries. This association defines a plurality of interfaces. Each interface corresponds to a different molecular size fraction of charged particles. The collecting means permits passage of charged particles, as when the directional electrophoretic gradient is imposed, when the charged particles are smaller than the molecular size fraction to which the particle interface correspond, but collects charged particles at that interface when the particles are larger than the molecular size fraction to which the interface correspond.

A preferred embodiment is wherein the gel matrixes are in a non-contiguous relationship with the interfaces being interposed therebetween and the gel matrixes are formed with differing concentrations of agarose and agarose derivatives so that the gel matrixes are of a consecutively decreasing pore size from a most upstream matrix to the most downstream matrix.

DESCRIPTION OF THE INVENTION

We have invented a device and method particularly useful in rapidly and simply separating a cholesterol sample into its HDL, LDL, VLDL, and chylomicron fractions such that each fraction becomes readily available for rapid analysis of its cholesterol content by conventional enzymatic methods. The method is simple, such that it may be carried out in an office or field environment without laboratory facilities. Alternately, it can provide separated fractions in a field or office environment for subsequent analysis in a laboratory.

In its simplest form, the device of this invention incorporates a multiplicity of distinct polymer gels, or gel matrixes, of successively decreasing porosity arranged in a series such that charged particles, such as macromolecules, of different molecular or particle size tend, under an electrophoretic field, to migrate through each successive gel until a gel is reached whose pores are small enough to restrict further mobility of the macromolecule or particle. Thus, after a time, any charged macromolecules contained in the sample tend to separate into distinct groups by size with each separate gel compartment containing materials of a distinct molecular or particle size range.

A preferred embodiment is where a four-compartment system is constructed in which a serum sample containing cholesterol may be fractionated into four distinct gel compartments under an electrophoretic field with HDL-, LDL-, VLDL-, and chylomicron cholesterol fractions being separately deposited, each into its respective gel compartment.

The particularly preferred embodiment of the invention is where a multiplicity of liquid buffer zones are each in contact with one of gel zones and in electrical contact with the electrophoretic gradient such that any charged macromolecules imbedded in the edge of that particular gel can be quickly stripped into solution by reversal of the electrophoretic field facilitating removal of the separated fractions from the device which may be accomplished by removing each liquid buffer zone via pipet. Alternatively, by insertion of collection media, e.g. absorbent paper or cellulosic membrane, into the buffer zone followed by reversal of the electrophoretic voltage, the separated components which have been concentrated into the edge of each gel compartment can migrate into the buffer liquid and are sorbed on the collection media placed in that buffer compartment.

The diagnostic device of the invention includes a cathode and an anode. A liquid pathway is defined between the cathode and anode upon which a directional electrophoretic gradient can be imposed either from the cathode to anode or visa versa (when current is reversed). Means for introducing liquid sample into the liquid pathway adjacent to cathode is provided, such as a sample well and a separator, which isolate the sample from the cathode.

A plurality of gel matrixes (preferably four when the device is desired for use to separate the four cholesterol fractions) are in a serial relationship one to the other with one being upstream relative to a downstream other. Each gel matrix defines a boundary, normally substantially planar, that is generally transverse to the liquid pathway.

Use of the term "charged particles" with which the diagnostic device is useful is meant to include a variety of molecules having different molecular weights and ranging from relatively small ions to macromolecular aggregates such as the different lipoprotein cholesterol fractions. The number of gel matrixes will be determined by the number of different charged particle fractions one desires to separate.

Gel matrixes are preferably formed from agarose and agarose derivatives, most preferably from agarose and agarose derivatives in differing concentrations, although minor amounts of other components (such as, for example, hydroxyethylcellulose) can be included. Particularly preferred agarose derivatives for fractionating lipoproteins include hydroxyethylated agarose.

Agarose is a natural polysaccharide isolated from agar, and agarose gel is a relatively transparent anticonvection medium that tends to prevent broadening during electrophoretic separations. Agarose is essentially biologically inert and non-toxic and is generally considered the medium of choice for separation by molecular weight of large macromolecules and for resolving nucleic acids. Agarose forms firm, mechanically stable gels even at relatively low concentrations and yields a macroporous matrix. These properties of gel strength and macroporosity are possible because, during gelation, agarose molecules associate into double helices which then further aggregate to form a rigid matrix of suprafibers. A general description of interest pertaining to agarose is by Serwer, "Agarose Gels: Properties and Use for Electrophoresis", *Electrophoresis*, Vol. 4, pp. 375-382 (1983). Sieving in agarose is dependent on a gel concentration and can be increased by increasing the percentage of agarose in the gel. Derivatization of agarose (such as by hydroxyethylation) has been observed to increase the sieving properties. It has been proposed that hydroxyethylation causes a decrease in the number of agarose double helices per suprafiber resulting in reduced pore sizes by Serwer et al., "Agarose Gel Electrophoresis of Bacteriophages and Related Particles . . . ", *Electrophoresis*, Vol. 4, pp. 233-236 (1983).

In addition to additives such as hydroxyethycellulose, to gel matrixes of the invention, other possible additives include methylcellulose, hydroxypropylcellulose, and acrylic polymers. Appropriate amounts of such additional components are in a range of from about 1-20 wt. % basis with respect to agarose.

The inventive diagnostic device further includes collecting means disposed in the liquid pathway and associated with the gel matrix boundaries. The collecting means defines a plurality of interfaces between the gel matrixes. Each interface corresponds to a different molecular size fraction of charged particles. The collecting means permits passage of charged particles through a particular one of interfaces when the charged particles are smaller than the molecular size fraction to which that interface correspond and collecting means is further for collecting charged particles at the particular interface when the charged particles are larger than the molecular size fraction to which the interface correspond.

In the simplest version of diagnostic device there will be substantial identity between each of the gel matrix boundaries and a respective each of the interfaces. In one embodiment the gel matrixes will be in a contiguous relationship but with a more upstream gel matrix being of an increased pore size with respect to a more downstream gel matrix.

However, in a particularly preferred embodiment for diagnostic device, the gel matrixes will be in a non-contiguous relationship, and the interfaces can be viewed as interposed between the gel matrixes.

Thus, for example, the interfaces can include discrete compartments. These compartments are adapted to contain only liquid (rather than the two phase system of the gel matrixes). This liquid is typically buffer compatible with the liquid sample being fractionated.

Each of compartments is of a suitable construction to receive a separate lipoprotein fraction that will typically have sorbed on respective interfaces, but which desorb upon reversal of the electrophoretic gradient direction. The fourth cholesterol fraction will, however, be "sorted" and can be retrieved at the boundary adjacent to the sample well.

For a particular separation of species W, X, Y, and Z, each being successively smaller in molecular diameter, a first gel would be selected as having a porosity such that passage of W would be restricted, but X, Y, and Z would quickly pass through, the next gel would be selected to stop passage of W and X but to pass Y and Z, and so on. Under an electrophoretic field, then, the species would all begin to migrate from the sample well successively toward the anode with W being stopped in the edge of the first gel, X being stopped in the edge of the next gel, Y being stopped in the third gel, and Z being stopped in the last gel.

For example, it has been demonstrated that HDL, LDL, VLDL, and chylomicron cholesterol can be separated in this manner when the first gel was made from a 1% w/w agarose solution and the remaining gels each were, respectively, made from increasingly higher concentration of hydroxyethylated agarose solution ranging from about 2-8% w/w. A similar effect can be obtained with gels made by blending hydroxyethylcellulose with agarose solutions.

Buffers may be selected, as is known in the art, to maximize the electrophoretic mobility of species in an electrophoretic field. For the separation of HDL, LDL, VLDL, and chylomicron cholesterol, tris(hydroxymethyl)-aminomethane borate buffer or land 2(N-cyclohexylamino)ethane sulfonic acid buffer adjusted to pH 8.9 have been found to be acceptable.

The size of the electrophoresis cell, or device, is important and it is desirable that dimensions be minimized. To minimize heat generation, thickness of the gel slabs in at least one dimension should be less than 2 mm and preferably between 0.1-1.0 mm. The length of the cell parallel to the electrophoretic field is important. A distance of 0.5-5.0 mm length for each gel is necessary to provide the necessary separating power and to allow for manufacturability, while further increases only add to the time of analysis. The cross-sectional area of the gel slab normal to the electrophoretic field has no direct effect on separating power but controls the amount of sample which may be applied. In this regard, a cross-section of 2.0-100 mm$^2$ has been found to be functional.

The device of this invention may be further designed as a molded or thermoformed plastic assembly containing the compartments described so that each separated cholesterol fraction is separately conducted to a separate chamber containing the means for performing a quantitative analysis for cholesterol by conventional methods.

In its simplest form, such a chamber incorporates a surface active agent, which is required to denature the cholesterol particle, cholesterol esterase which is required to liberate cholesterol from its naturally-occurring ester form, cholesterol oxidase which generates one mole of hydrogen peroxide from each mole of cholesterol present, and a chromogenic substrate with peroxidase which develop a color proportional to the quantity of peroxide generated, hence proportional to the quantity of cholesterol present.

The quantity of HDL-, LDL-, VLDL-, and chylomicron cholesterol present can be determined by viewing the colors generated or by reading the developed colors with a suitable photometric instrument.

Such devices for performing a rapid quantitative analysis of cholesterol, once the HDL-, LDL-, VLDL-, and chylomicron factors have been separated, are within the state of the art and are commercially available from a variety of sources.

Turning to FIG. 1, a simple diagnostic device 10 embodying the invention is illustrated. Cathode 12 and anode 14 are associated with conventional electrical circuitry (not illustrated). Device 10 is formed by a body 16 which may be tubular and may be comprised of a variety of materials, such as, for example, acrylic. Dotted line 18 illustrates the liquid pathway formed through body 16 from a one end, or top, 16a to another end, or bottom, 16b. Means for introducing sample into device 10 are achieved here by an orifice 20 communicating with sample well 22. During operation, a sample will be applied at the bottom 26 of sample well 22 and buffer will be added into sample well 22. An adjacent chamber 24 has vent 28 (to vent hydrogen gas formed during electrophoresis).

A plurality of gel matrixes 30a, 30b, 30c, and 30d are disposed along flow path 18 with alternating compartments 32a, 32b, 32c, and 32d. Gel matrixes 30a–d may be formed in the "spool" shape shown with radially outward opposed flanges 34, 36 interconnected by neck 38. Neck 38 is, of course, part of liquid pathway 16. Screens 35, 37 function as supports, or substrates, upon which flanges 34, 36 are supported. Flanges 34, 36 and neck 38 together are formed of gel. Flanges 34, 36 assist in preventing leakage between compartments.

Access ports 40a–c provide access into compartments 32a–c respectively. For example, analysis by use of conventional dip sticks of the separated fractions through access ports 40a–c may be accomplished.

EXAMPLE 1

Illustrative Components of Separation System

The following description is meant to illustrate the preparation of a preferred series of gel matrixes 30 with appropriately decreased porosity as one moves down liquid pathway 18 in a device in accordance with the invention.

(1) Prepare warm solutions of the following gels:
(a) Agarose, 1% w/w in buffer;
(b) Hydroxyethylated Agarose, 2% w/w in buffer;
(c) Hydroxyethylated Agarose, 5% w/w in buffer; and
(d) Hydroxyethylated Agarose, 8% w/w in buffer.

(2) a trough and molds for holding the gels as shown in FIG. 1.

(3) Pour heated gel from step 1(a), above, into compartment 30a, gel from step 1(b) into position 30b, gel from 1(c) into position 30c, and gel from step 1(d) into position 30d, by reference to FIG. 1.

(4) Fill buffer liquid compartments 32a, 32b, and 32c and the compartments 22 and 24, respectively, with buffer solution.

EXAMPLE 2

Illustrative Method for Cholesterol Profile Separation (1) Add sample containing 0.01–0.20 μl of blood serum to sample compartment 19 of device prepared according to Example 1.

(2) Using an appropriate DC voltage source, apply 50–500 volts across the electrodes for 10–50 minutes.

Proceed either to step (6)(a), (6)(b), or (6)(c).

(3)(a) After electrophoresis is complete, remove each gel slab from its respective position and perform cholesterol analysis directly on the surface of the gel by dipping the gel into cholesterol reagent mixtures.

(3)(b) After electrophoresis is complete, reverse the applied field for 0.1–5 minutes to cause species to migrate out of the edge of the gel and into an adjacent buffer solution. Analyze an aliquot of the buffer solution for cholesterol by conventional methods.

(3)(c) After electrophoresis is complete, remove each slab from its respective position, dissolve or melt the gel, then analyze an aliquot of the resulting solution for cholesterol by conventional methods.

EXAMPLE 3

Data Demonstrating Separation of Cholesterol Components

An assembly similar to that shown in FIG. 1 was prepared by successively casting a series of gels including a 1% agarose (gel 30a), 2% hydroxyethylagarose (gel 30b), 5% hydroxyethylagarose (gel 30c), and 8% hydroxyethylagarose (gel 30d), respectively, in a tube with buffer compartments 32a, 32b, and 32c adjacent to gels 30a, 30b, 30c, and 30d. A 100 microliter aliquot of human serum stained with Sudan Black B, a specific stain for lipid molecules, was pipetted into sample well 22. The cathode and anode compartments 24 and 32d were filled with the same buffer as compartments 28a, 28b, and 28c.

220 volts were applied across the cell generating approximately 3 ma of current which was sustained for 15 minutes. After 15 minutes, electrophoresis was discontinued and the cell upon examination contained four distinct, blue bands in each of the four gels. The bands in gels 30a, 30b, and 30c were sharp (approximately 0.1 mm in thickness) and were located at the extreme edge of the gels nearest to the cathode. The band in gel 30d was approximately 0.2 mm in thickness and was located part of the way through the gel toward the anode.

The conditions of the above electrophoresis were repeated in three separate experiments sequentially in which the serum sample was replaced successively by an authentic sample containing, respectively, HDL cholesterol, LDL cholesterol, and VLDL cholesterol. After the HDL cholesterol sample was electrophoresed for 15 minutes the blue stain appeared in a concentrated band approximately 0.2 mm in thickness and approximately ⅓ of the distance from the cathodic side of gel 30d. After the LDL cholesterol sample was electrophoresed for 5 minutes, the blue stain appeared in a narrow 0.1 mm band at the extreme cathodic edge of gel 30c. After VLDL cholesterol was electrophoresed for 15 minutes, the blue stain appeared in a narrow 0.1 mm band at the extreme cathodic edge of gel 30b.

The conditions of electrophoresis above were again repeated with a serum sample except that the blue stain was not added. At the conclusion of electrophoresis a paper strip was placed in each of buffer compartments 32a, 32b, and 32c and the voltage was reversed (i.e. the cathode was made the anode, and vice-versa) for 3 minutes. After this time, each paper strip was removed and placed in contact with reagent paper for testing cholesterol obtained from commercial sources. The sample paper was placed in contact with the reagent paper and incubated at 37° C. in a humid environment for 10 minutes and examined. After the incubation, the reagent paper gave a bright red stain indicating the recovery of significant quantities of cholesterol.

FIG. 2 illustrates another embodiment of the invention that is somewhat more elaborate than the embodiment illustrated by FIG. 1 and already described. Device 100 has cathode 112 and anode 114, again in electrical communication by conventional means not illustrated. Body 116 defines top 116a and bottom 116b with liquid pathway being illustrated by dashed line 118. Sample is introduced into body 116 through orifice 120 into sample well 122b (via chamber 122a) along sample well bottom surface 126. Gel matrixes 130a–d are analogous to the gel matrixes 30a-d of the other embodiment except that gel matrix 130d need not include an upper flange, but rather may simply have an upper screen 135. Alternatively, the entire gel matrix 130d can have substituted a filter (not illustrated) or can use both a filter and a gel body. This is because as the terminal, or last, interface at which HDL collects (when conducting an assay of cholesterol fractions) have all the HLD stopped by a filter.

Embodiment 100 also has compartments 132a-d, which are analogous to the previously described compartments 32a-d. However, each of compartments 132a-c (and also sample well 122b) has pH adjusting means 142a, 144a, 146a, and 148a, respectively, for introducing a pH adjusting solution into the corresponding well or compartments (after having performed the electrophoretic separation operation). Also adjacent to sample well 122b and compartments 132a-c, respectively, are reagent wells 142b, 144b, 146b, and 148b. Each pH adjusting means and its corresponding reagent (e.g., 142a, b, and so forth) together comprise analysis means for performing quantitative analysis of cholesterol (such as through enzymatic color changes), once the different factors have been separated.

In operation, once separation has been completed, plunger 150 is moved so as to cause the advance of needles 152a, 154a, 156a, and 158a through corresponding diaphragms 160. This permits the pH adjusting solution to flow into an adjacent well or compartment by means of the pierced diaphragms 160.

Meanwhile, movement of the plunger 150 has also advanced plungers 162b, 168b beyond each corresponding reagent well 142b-148b. Thus, when the reagent wells each contain selected powder reagent (from commercially available ingredients in appropriate formulations known to the art) an in situ diagnostic solution for each separated cholesterol fraction is formed, which may be analyzed by means such as directing a visible light beam through each respective compartment, provided the device is manufactured of a optically clear plastic such as polystyrene or polymethylmethacrylate, and measuring the degree of light absorption by the solution in each respective compartment.

It is to be understood that while the invention has been described above in conjunction with preferred specific embodiments, the description and examples are intended to illustrate and not limit the scope of the invention, which is defined by the scope of the appended claims.

We claim:

1. A diagnostic apparatus useful for electrophoretic fractionation of charged particles having different molecular weights within a liquid sample comprising:
   a plurality of gel matrixes defining a liquid pathway upon which a directional electrophoretic gradient can be imposed and each gel matrix defining a boundary generally transverse to the fluid pathway, the gel matrixes being in a serial relationship with a one being upstream relative a downstream other;
   means for introducing the liquid sample into the liquid pathway upstream of the one gel matrix; and,
   a plurality of collecting means disposed in the liquid pathway and associated with the gel matrix boundaries, the collecting means defining a plurality of interfaces between the gel matrixes, the interfaces each corresponding to a different molecular size fraction of charged particles, the collecting means for permitting passage of charged particles through an interface when the charged particles are smaller than the molecular size fraction to which that interface corresponds and for collecting charged particles at that interface when the charged particles are larger than the molecular size fraction to which the interface corresponds.

2. The diagnostic apparatus as in claim 1 wherein the gel matrixes are in a noncontiguous relationship, and the interfaces of the collecting means are interposed between the gel matrixes.

3. The diagnostic apparatus as in claim 2 wherein the interfaces include discrete compartments containing a single, liquid phase.

4. The diagnostic apparatus as in claim 3 wherein the plurality of gel matrixes are adapted to permit or prevent passage of charged particles by preselected, differing porosities of the gel matrixes.

5. The diagnostic apparatus as in claim 1 wherein at least some of the interfaces are formed by contiguous boundaries between gel matrixes of differing porosities.

6. The diagnostic apparatus as in claim 2 or 5 wherein the gel matrixes include agarose and agarose derivatives.

7. The apparatus as in claim 6 wherein the gel matrixes are formed with differing concentrations of agarose and agarose derivatives.

8. An electrophoretic apparatus useful for sorting seric or plasmatic lipoproteins within a liquid sample into chylomicron-, VLDL-, LDL- and HDL-cholesterol fractions, comprising:
   four agarose-based matrixes defining a liquid pathway upon which a directional electrophoretic gradient can be imposed and each matrix defining a substantially planar boundary generally transverse to the fluid pathway, the gel matrixes being in a serial relationship and being of a successively decreasing pore size from a most upstream matrix to the most downstream matrix;
   means for introducing the liquid sample into the liquid pathway upstream of the most upstream gel matrix; and,
   four collecting means disposed in the liquid pathway and each associated with a different each of the matrix boundaries, at least three of the collecting means defining three interfaces between three of the gel matrixes, each of the collecting means for collecting a different fraction of lipoprotein adjacent to a boundary.

9. The electrophoretic apparatus as in claim 8 wherein the matrixes are in a noncontiguous relationship with the three interfaces interposed between and separating the three most downstream gel matrixes.

10. The electrophoretic apparatus as in claim 9 wherein the interfaces include discrete compartments containing buffer.

11. The electrophoretic apparatus as in claim 9 wherein the three interfaces are adapted each to receive a separate lipoprotein fraction upon reversal of the electrophoretic gradient direction.

12. The electrophoretic apparatus as in claim 8 wherein the matrixes are formed from agarose, hydroxyethylated agarose, hydroxyethylcellulose, and mixtures thereof.

* * * * *